US010081651B2

(12) United States Patent
Eilers et al.

(10) Patent No.: US 10,081,651 B2
(45) Date of Patent: Sep. 25, 2018

(54) CHLORINATION OF SUCROSE-6-ESTERS

(71) Applicant: Tate & Lyle Technology Limited, London (GB)

(72) Inventors: Thomas Eilers, Arlington Heights, IL (US); Halil Aktas, NB Zaandam (NL)

(73) Assignee: Tate & Lyle Technology Limited, London (GB)

( * ) Notice: Subject to any disclaimer, the term of this patent is extended or adjusted under 35 U.S.C. 154(b) by 0 days.

(21) Appl. No.: 15/502,372

(22) PCT Filed: Jun. 16, 2015

(86) PCT No.: PCT/GB2015/051758
§ 371 (c)(1),
(2) Date: Feb. 7, 2017

(87) PCT Pub. No.: WO2016/020635
PCT Pub. Date: Feb. 11, 2016

(65) Prior Publication Data
US 2017/0233424 A1 Aug. 17, 2017

Related U.S. Application Data

(60) Provisional application No. 62/035,066, filed on Aug. 8, 2014.

(51) Int. Cl.
C07H 5/02 (2006.01)
C07H 13/04 (2006.01)

(52) U.S. Cl.
CPC .............. C07H 5/02 (2013.01); C07H 13/04 (2013.01)

(58) Field of Classification Search
None
See application file for complete search history.

(56) References Cited

U.S. PATENT DOCUMENTS

| | | | |
|---|---|---|---|
| 4,380,476 A | 4/1983 | Mufti et al. |
| 4,889,928 A | 12/1989 | Simpson |
| 4,950,746 A | 8/1990 | Navia |
| 4,980,463 A | 12/1990 | Walkup et al. |
| 5,023,329 A | 6/1991 | Neiditch et al. |
| 5,034,551 A | 7/1991 | Vernon et al. |
| 5,089,608 A | 2/1992 | Walkup et al. |
| 5,298,611 A | 3/1994 | Navia et al. |
| 5,440,026 A | 8/1995 | Khan et al. |
| 5,470,969 A | 11/1995 | Sankey et al. |
| 5,498,709 A | 3/1996 | Navia et al. |
| 5,530,106 A | 6/1996 | Navia et al. |
| 5,977,349 A | 11/1999 | Catani et al. |
| 6,646,121 B2 | 11/2003 | El Kabbani et al. |
| 6,809,198 B2 | 10/2004 | El Kabbani et al. |
| 6,890,581 B2 | 5/2005 | Vernon et al. |
| 6,939,962 B2 | 9/2005 | Clark et al. |
| 6,943,248 B2 | 9/2005 | Catani et al. |
| 6,998,480 B2 | 2/2006 | Catani et al. |
| 7,049,435 B2 | 5/2006 | Catani et al. |
| 7,932,380 B2 | 4/2011 | Hao |
| 8,212,022 B2 | 7/2012 | Micinski et al. |
| 2006/0188629 A1 | 8/2006 | Liesen et al. |
| 2006/0205936 A1 | 9/2006 | Jia et al. |
| 2006/0276639 A1 | 12/2006 | Fry |
| 2007/0015916 A1 | 1/2007 | Kabbani et al. |
| 2007/0100139 A1 | 5/2007 | Fry |
| 2007/0160732 A1 | 7/2007 | Deshpande et al. |
| 2007/0227897 A1 | 10/2007 | Li et al. |
| 2007/0270583 A1 | 11/2007 | Ratnam et al. |
| 2011/0087018 A1 | 4/2011 | Micinski et al. |
| 2012/0077972 A1 | 3/2012 | Boutzale et al. |
| 2012/0095199 A1 | 4/2012 | Hutton et al. |

FOREIGN PATENT DOCUMENTS

| | | |
|---|---|---|
| EP | 0409549 A2 | 1/1991 |
| EP | 0708110 A2 | 4/1996 |
| GB | 2471348 A | 12/2010 |
| WO | 2007099557 A2 | 9/2007 |
| WO | 2010109189 A1 | 9/2010 |
| WO | 2010112813 A1 | 10/2010 |
| WO | 2010151489 A1 | 12/2010 |
| WO | 2011045565 A1 | 4/2011 |
| WO | 2012071385 A1 | 5/2012 |
| WO | 2013056128 A1 | 4/2013 |
| WO | 2015092374 A1 | 6/2015 |

OTHER PUBLICATIONS

Zofia Mielke et al., Infrared Matrix Isolation Studies of Complexes between N,N-Dimethylacetamide and Hydrogen Halides, Part 1.—Hydrogen Chloride and Hydrogen Bromide Complexes, J. Chemical Society, Faraday Trans. 2, 1986, vol. 82, pp. 437-446.
International Search Report for International Application No. PCT/GB2015/051758, dated Oct. 20, 2015, 5 pages.
International Preliminary Report on Patentability and Written Opinion for International Application No. PCT/GB2015/051758, dated Feb. 14, 2017, 8 pages.

Primary Examiner — Layla D Berry
(74) Attorney, Agent, or Firm — RatnerPrestia

(57) ABSTRACT

There is provided a method for the chlorination of a sucrose-6-acylate to produce a 4,1',6'-trichloro-4,1',6'-trideoxy-galactosucrose-6-acylate, wherein said method comprises the following steps (i) to (v): (i) providing a first component comprising sucrose-6-acylate; (ii) providing a second component comprising a chlorinating agent; (iii) combining said first component and said second component to afford a mixture; (iv) heating said mixture for a heating period in order to provide chlorination of sucrose-6-acylate at the 4, 1' and 6' positions thereof; (v) quenching said mixture to produce a 4,1',6'-trichloro-4,1',6'-trideoxy-galactosucrose-6-acylate; wherein at least one of said first component and said second component comprises a reaction vehicle, and said reaction vehicle comprises a tertiary amide; and wherein said mixture comprises a cosolvent during a least a portion of the heating period of step (iv), wherein said cosolvent comprises dimethylacetamide (DMAc).

11 Claims, 1 Drawing Sheet

CHLORINATION OF SUCROSE-6-ESTERS

CROSS-REFERENCE TO RELATED APPLICATIONS

This is the national phase of International Application No. PCT/GB2015/051758, filed 16 Jun. 2015, which claims priority to U.S. Provisional Application No. 62/035,066, filed 8 Aug. 2014. The disclosure of each of these applications is incorporated herein by reference in its entirety for all purposes.

TECHNICAL FIELD

The present invention relates to an improved method for the production of sucralose. In particular, the present invention relates to a method for the chlorination of a sucrose-6-acylate to afford a sucralose-6-acylate. Sucrose-6-acylate and sucralose-6-acylate are important intermediates in the production of sucralose.

BACKGROUND

Methods for producing sucralose intermediates and sucralose from a feed stream comprising a sucrose-6-acylate in a reaction vehicle are known. For example, EP 0409549 discloses a process for the chlorination of a sucrose-6-acylate in a tertiary amide reaction vehicle to produce a sucralose-6-acylate, such as sucralose-6-acetate. A large excess of an acid chloride, such as phosgene, is used as the chlorination agent in this process. Following the chlorination reaction, the excess chlorinating agent is quenched using a suitable base, thereby forming the chloride salt of the base. The resulting product stream thus comprises a sucralose-6-acylate, the tertiary amide reaction vehicle, water, and salts.

A known method for obtaining sucralose from a product stream comprising a sucralose-6-acylate, a tertiary amide reaction vehicle, water, and salts, without isolation of the sucralose-6-acylate intermediate, is disclosed in EP 0708110. The process comprises deacylation of the sucralose-6-acylate before or after removal of the tertiary amide reaction vehicle, and then isolation of the sucralose. The removal of the tertiary amide (which is usually dimethylformamide [DMF]) is carried out by steam stripping. Other methods of extraction of sucralose are known, for example, in U.S. Pat. No. 8,212,022.

Methods for preparing sucrose-6-acylate starting materials for chlorination to sucralose-6-acylate are known, for example, in U.S. Pat. No. 4,950,746; U.S. Pat. No. 4,889,928; U.S. Pat. No. 5,023,329; U.S. Pat. No. 5,089,608; U.S. Pat. No. 5,034,551; U.S. Pat. No. 5,470,969; U.S. Pat. No. 5,440,026; U.S. Pat. No. 6,939,962; and US 2007-0227897.

Other methods of chlorinating sucrose-6-acylate to give sucralose-6-acylate are known, for example, in U.S. Pat. No. 4,380,476; US 2006-0205936; U.S. Pat. No. 7,932,380; and US 2007-0100139.

When a tertiary amide such as DMF is used as a reaction solvent for chlorination, it is known to include a co-solvent in the reaction medium, for example, in US 2011-087018; WO 2011-045565; US 2012-0077972; and US 2012-0095199; as well as in EP 0409549.

Further methods of chlorinating carbohydrates such as sucrose-6-acylates are known in WO 2012/071385 and WO 2013/056128. These two documents disclose a variety of solvents and co-solvents for the chlorination of carbohydrates.

Although methods of making sucralose, and of chlorinating sucrose-6-acylate to give sucralose-6-acylate, are known, there may remain scope to modify the chlorination reaction.

SUMMARY

According to a first aspect of the present invention, there is provided:
1) a method for the chlorination of a sucrose-6-acylate to produce a 4,1',6'-trichloro-4,1',6'-trideoxy-galactosucrose-6-acylate, wherein said method comprises the following steps (i) to (v):
(i) providing a first component comprising sucrose-6-acylate;
(ii) providing a second component comprising a chlorinating agent;
(iii) combining said first component and said second component to afford a mixture;
(iv) heating said mixture for a heating period in order to provide chlorination of sucrose-6-acylate at the 4, 1' and 6' positions thereof;
(v) quenching said mixture to produce a 4,1',6'-trichloro-4,1',6'-trideoxy-galactosucrose-6-acylate;
wherein at least one of said first component and said second component comprises a reaction vehicle, and said reaction vehicle comprises a tertiary amide; and
wherein said mixture comprises a cosolvent during a least a portion of the heating period of step (iv), wherein said cosolvent comprises N,N-dimethylacetamide (DMAc).
There is further provided:
2) a method according to 1), wherein both of said first component and said second component comprise said reaction vehicle;
3) a method according to 1) or 2), wherein said cosolvent additionally comprises sulfolane and/or perfluorooctane;
4) a method according to any of 1) to 3), wherein said cosolvent is added to the mixture after step (iii) and before step (iv);
5) a method according to any of 1) to 3), wherein said cosolvent is added to the mixture during step (iv);
6) a method according to 5), wherein the cosolvent is added once the mixture temperature is greater than or equal to about 55° C.;
7) a method according to 3) wherein the DMAc portion of the cosolvent is added to the mixture after step (iii) and before step (iv) and/or during step (iv); and the perfluorooctane and/or sulfolane is present in the first and/or second components, and/or is added during step (iii);
8) a method according to 7) wherein the DMAc is added to the mixture during step (iv) once the mixture temperature is greater than or equal to about 55° C.;
9) a method according to any of 1) to 8), wherein said cosolvent consists of DMAc, DMAc and perfluorooctane, DMAC and sulfolane or DMAc, perfluorooctane and sulfolane.
10) a method according to any of 1) to 9), wherein said reaction vehicle comprises dimethylformamide (DMF).
11) a method according to 10), wherein said reaction vehicle consists of dimethylformamide (DMF).
There are further provided methods which further comprise the step of converting at least a portion of said 4,1',6'-trichloro-4,1',6'-trideoxy-galactosucrose-6-acylate to sucralose; and of isolating and purifying the sucralose.

Further features and advantages of the invention will become apparent from the following description of preferred embodiments of the invention, given by way of example only, which is made with reference to the accompanying drawings.

DETAILED DESCRIPTION

Figure 1:
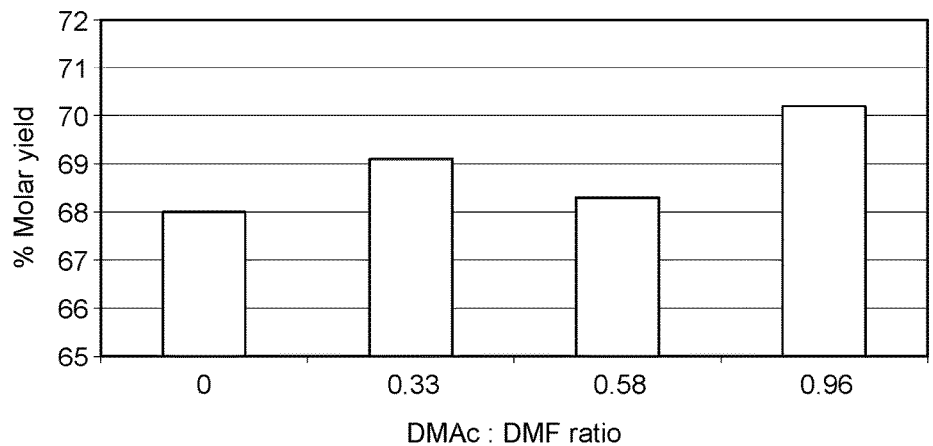
FIG. 1 shows the effect of ratio by weight of DMAc to dimethylformamide (DMF) on sucralose yield.

A 4,1',6'-trichloro-4,1',6'-trideoxy-galactosucrose-6-acylate can also be referred to as a sucralose-6-acylate, so that 4,1',6'-trichloro-4,1',6'-trideoxy-galactosucrose-6-acetate can also be referred to as sucralose-6-acetate. Both terminologies are used herein.

The sucrose-6-acylate can be any acylate that serves to protect the 6-hydroxy group during the chlorination reaction. It is preferably an aliphatic or carbocyclic aromatic acylate, more preferably a benzoate or acetate, and most preferably an acetate.

As used herein, the term "reaction vehicle" means the diluent or solvent in which the chlorination reaction is performed. The term is meant to indicate that the vehicle may not fully dissolve all the components of the reaction and product mixture. Depending on the chlorinating agent employed, a number of types of reaction vehicles may be used, and any reaction vehicle can be used that is stable under the chlorination conditions and that dissolves the starting materials, reagents, and products at least to some extent. The reaction vehicle according to the present invention comprises a tertiary amide. The tertiary amide reaction vehicle is preferably DMF. The ratio by weight of the tertiary amide reaction vehicle, for example DMF, to total carbohydrate during the chlorination reaction may be from about 1.8:1 to about 13:1, or from about 2.5:1 to about 8:1.

For the avoidance of doubt, in the above "reaction vehicle" is not included any portion that reacts with the chlorinating agent. For example, if the chlorinating agent is Arnold's reagent and the reaction vehicle is DMF, even if the chlorinating agent is added as phosgene which reacts in situ to form Arnold's reagent, those equivalents of DMF are not included in the weight of reaction vehicle for calculating the ratio to carbohydrate.

The first component and/or the second component may be provided in the reaction vehicle.

A number of chlorinating agents may be used in the present invention in order to chlorinate the 4, 1' and 6' positions of the sucrose-6-acylate. Suitable examples include those selected from the group consisting of phosgene, Arnold's reagent (also known as (chloromethylene) dimethyliminium chloride or as (chloromethylene)dimethylammonium chloride), phosphorous oxychloride, phosphorous pentachloride, thionyl chloride, oxalyl chloride, methanesulfonyl chloride, sulfuryl chloride, diphosgene (trichloromethyl chloroformate) and triphosgene (bis (trichloromethyl) carbonate). Other suitable chlorinating agents known to the skilled person may also be used. Preferably, the chlorinating agent is phosgene or Arnold's reagent.

The chlorinating agent is preferably in excess with respect to the sucrose-6-acylate, and preferably in large excess. At least three molar equivalents of chlorinating agent are required per mole of sucrose-6-acylate in order to chlorinate the 4, 1' and 6' positions; thus, an excess amount of chlorinating agent is any amount above three molar equivalents per mole. In a preferred embodiment, the chlorinating agent is provided in an amount of at least seven molar equivalents per mole of the sucrose-6-acylate. Typically, the molar ratio of the chlorinating agent to the sucrose-6-acylate is about 7:1 to about 11:1.

The first component and the second component are combined in step (iii). This is typically conducted at a temperature of from −15 to 55° C., preferably at a temperature of from 0 to 20° C. A typical temperature is 5° C.

When the first component and the second components are combined, the chlorinating agent reacts with the unprotected hydroxyl groups on the sucrose-6-acylate. This is conveniently referred to as "first stage chlorination". For example, when the chlorinating agent is Arnold's reagent, an adduct is formed. The adduct is shown schematically as formula 3 in FIG. 2 of U.S. Pat. No. 4,980,463, which refers to the adduct as "O-alkylformiminium chloride intermediate". This reaction is rapid at around 5° C. Therefore, the time of holding the resulting mixture is not particularly limited. It may be a few minutes, for example from 5 to 30 minutes, or up to several hours, for example from 5 minutes to 24 hours.

The mixture is then heated to achieve chlorination of sucrose-6-acylate at the 4, 1' and 6' positions thereof in step (iv). This is conveniently referred to as "second stage chlorination". In this process, the adduct is converted into the corresponding chloride. At the 4-position of the sucrose adduct, predominant inversion of stereochemistry occurs.

A number of reaction conditions can be used to achieve the chlorination. Walkup, U.S. Pat. No. 4,980,463, the disclosure of which is incorporated herein by reference, for example, discloses a two stage process in which chlorination is carried out at two different temperatures, a temperature not higher than about 85° C. and a temperature of at least about 100° C. but not higher than about 130° C. to effect chlorination. Fry, U.S. 2007/0100139, the disclosure of which is incorporated herein by reference, discloses a process in which the reaction mixture is heated between 75° C. to 100° C. to effect chlorination.

In general, the reaction temperature for the chlorination reaction is typically from 85° C. to 130° C. A typical temperature is from 95° C. to 100° C.

The reaction time for the chlorination depends on the temperature employed, with lower temperatures requiring longer reaction times. The skilled person can easily determine the optimum reaction time for a given reaction temperature by monitoring the reaction. If the reaction time is too short, insufficient conversion to the 4,1',6'-trichloro-4, 1',6'-trideoxy-galactosucrose-6-acylate occurs. If the reaction time is too long, over-chlorination will occur, resulting in increased levels of tetra-chlorinated by-products. Typical reaction times are from 1 hour to 24 hours.

In the chlorination reaction, a cosolvent is present, and the cosolvent comprises N,N-dimethylacetamide (DMAc). As is disclosed in WO 2010/151489, DMAc reacts with chlorinating agent or otherwise interferes with first stage chlorination, so for the purposes of the present invention, it is not possible to have the DMAc present in the first and/or the second component, or to add it during the combination of the first and second components. However, once the first stage chlorination has proceeded, it has now been found that the presence of DMAc is not disadvantageous, and in fact has a beneficial effect on the chlorination reaction. Therefore, the DMAc is added after the two components are combined. If the cosolvent DMAc is present during the first stage chlorination reaction it will be consumed by a chlorinating agent such as phosgene or Arnold's reagent. The cosolvent is present during at least a portion of the heating period of step (iv). The cosolvent may be present during the whole of the heating period of step (iv).

Without wishing to be bound by theory, it is believed that cosolvent DMAc is ideally added once there is very little or no chlorinating agent present so that the DMAc (a) does not interfere in the first stage chlorination and (b) is not consumed by the chlorinating agent ensuring that it is available to act as a cosolvent. Generally, the cosolvent DMAc is added once there is very little or no chlorinating agent present, i.e. once the chlorinating agent has been substantially consumed/destroyed; this may be for example (a) after the chlorinating agent has been fully consumed in the first stage chlorination or (b) during the heating step, and at or above a temperature at which the chlorinating agent decomposes.

The cosolvent DMAc is present during at least a portion of the heating period of step (iv). The cosolvent DMAc may be present during the whole of the heating period of step (iv). The DMAc may be added once the mixture temperature exceeds a threshold value that may correspond to a temperature at which the chlorinating agent decomposes. In other words, the DMAc may be added during step (iv) once the mixture temperature is greater than or equal to a temperature at which the chlorinating agent decomposes. The DMAc may be added once the mixture temperature exceeds about 55° C., 60° C., 70° C., 80° C., 90° C. or 100° C. In embodiments in which the second component comprises Arnold's reagent as a chlorination agent, the DMAc may be added once the mixture temperature exceeds about 55° C., 60° C., 70° C., 80° C., 90° C. or 100° C. As noted above, DMAc is preferably added once the first stage chlorination is complete, and Arnold's reagent is believed to decompose at about 55° C. (in tertiary amide solvents), terminating the first stage chlorination. In particular, where the cosolvent comprises DMAc and one or more of perfluorooctane and sulfolane, the DMAc may be added once the mixture temperature exceeds about 80° C., 90° C. or 100° C.; without wishing to be bound by theory, it is thought that the decomposition temperature of the chlorinating agent may be higher when one or more cosolvent components such as perfluorooctane and/or sulfolane are present during the first stage chlorination.

In some embodiments, the DMAc may be added once the mixture temperature reaches the final temperature of the heating step (iv). In other word, the DMAc may be added once the mixture temperature reaches the temperature at which the second stage chlorination is substantially carried out.

By "cosolvent" is not meant any particular limitation, other than being a diluent or solvent, in addition to the reaction vehicle, in which the second stage chlorination reaction occurs. It should be compatible at least with the species present during second stage chlorination, and should not interfere with the second stage chlorination reaction.

The cosolvent may improve the efficiency and/or the yield of the reaction.

The addition of cosolvent DMAc in particular may reduce the overall degradation of DMF to dimethylamine, which occurs during second stage of chlorination reaction (See, for example, WO 2010/112813). DMAc is known to form 1:1 and 1:2 complexes with hydrogen chloride under at least some conditions (see, Zofia Mielke and Austin J. Barnes, J. Chem. Soc., Faraday Trans. 2, 1986, 82, 437-446 (DOI: 10.1039/F29868200437)). Without wishing to be bound by theory, it is possible that the effect of reduction of DMA formation that has been found when practising the present invention may be related to the formation of complexes with hydrogen chloride. Whatever the mechanism, it has been found, as shown later in the Examples, that quenched chlorinated product after chlorination in the presence of cosolvent DMAc exhibited less DMA than a control experiment without DMAc. The DMA in the quenched chlorinated product is generally inversely proportional to DMAc to DMF ratio.

The cosolvent comprises DMAc. The cosolvent may consist essentially of DMAc, or may consist solely of DMAc. Alternatively the cosolvent may additionally comprise one or more further compounds which have a cosolvent effect (such as improving the efficiency and/or the yield of the reaction). For example, the cosolvent may additionally comprise sulfolane and/or perfluorooctane. The cosolvent may consist essentially or consist solely of DMAc and perfluorooctane, DMAc and sulfolane or DMAC, perfluorooctane and sulfolane.

Where the cosolvent comprises more than one component, these may be added at different times. For example, sulfolane and/or perfluorooctane components may be provided in the first or second components, or may be added to the mixture during step (iii).

A further cosolvent component will typically be an aprotic solvent, and may be a polar aprotic solvent or an apolar aprotic solvent. A further cosolvent component may have a boiling point above 50° C., and may be miscible with the reaction vehicle and/or with the chlorination mixture.

The ratio by weight of the cosolvent (for example DMAc) to the reaction vehicle (for example DMF) may be from 0.1:1 to 3:1, or from 0.2:1 to 2:1, or from 0.3:1 to 1:1. The ratio is typically approximately 0.5:1.

The ratio of (reaction vehicle+cosolvent) to carbohydrate should preferably be less than 15:1. If reactions are performed more dilute than this then the yield may be adversely affected.

The reaction vehicle and the DMAc may be selected and presented in an amount such that the chlorination mixture during the heating period in step (iv) is homogeneous, or substantially homogeneous. Under some conditions, however, particularly if the ratio of DMF to DMAc is below a threshold value, the chlorination mixture may become heterogeneous as a slurry, namely a mixture having one liquid phase and one solid phase. Usually however the chlorination mixture will become homogeneous when the internal temperature is raised, for example, to above about 60° C. The reaction vehicle may be miscible with the cosolvent. In other embodiments, the reaction vehicle may be immiscible with the cosolvent, particularly if the cosolvent comprises perfluorooctane.

Once the chlorination reaction has proceeded to the desired stage of completion, there are a number of procedures that may be employed in order to quench the reaction, remove reaction vehicle and/or cosolvent, and take the material forward to produce sucralose.

If desired, a portion of the reaction vehicle and/or cosolvent may be removed directly from the mixture by distillation before quenching. The resulting distillate is typically made up primarily of the reaction vehicle comprising the tertiary amide and the cosolvent along with some acid (typically HCl, in particular when phosgene or Arnold's reagent is used as the chlorinating agent). The removal can be performed according to procedures described in WO 2010/109189, the disclosure of which is incorporated herein by reference in its entirety.

The reaction vehicle and/or cosolvent may be removed by distillation. This distillation may be conducted under reduced pressure, typically from 1 torr to 200 torr (0.13 to 26.7 kPa), or from 10 torr to 100 torr (1.3 to 13.3 kPa), or from 35 torr to 65 torr (4.7 to 8.7 kPa).

The removal of the reaction vehicle and/or cosolvent may be carried out at an internal temperature of from 40° C. to 150° C., or from 50° C. to 90° C. The removal of the tertiary amide can be carried out in a batch or continuous manner. In a batch manner, the removal of the tertiary amide may be carried out over a time period of from 1 hour to 24 hours. The temperature, pressure, and time required are interrelated, and optimum conditions can be determined by the person skilled in the art according to the operating requirements of the process and the equipment used. In general, the removal is carried out as rapidly as possible. If longer time periods are used for the removal, then lower temperatures will generally be used, in order to minimise carbohydrate degradation.

Following chlorination, whether or not any portion of the reaction vehicle and/or cosolvent is removed, the mixture may be quenched, for example with a base, to provide a sucralose-6-acylate and the acid salt of the base.

A number of different bases may be used in the quenching. Bases that can be employed for quenching include alkali metal or alkaline earth metal hydroxides, or ammonium hydroxide. As alkali metal hydroxides, sodium and potassium hydroxide are particularly suitable. As an alkaline earth metal hydroxide, calcium hydroxide is particularly suitable. The most usual base for quenching is sodium hydroxide, due to its ready availability and low cost. Other bases known to the skilled person may also be used for quenching. The quench may be performed with an aqueous solution of the base. The aqueous solution may contain from about 5 wt % to about 50 wt %, typically from about 8 wt % to about 40 wt % of the base. Within these ranges, the solution of the base can be either "concentrated" or "dilute". If the solution of the base is concentrated, then precipitation of salts is envisaged, and in this case suitable concentrations are from 13 to 50 wt %, or from 25 to 45 wt %, or about 35 wt %. If the solution of the base is dilute, precipitation of salts is not envisaged, and in that case suitable concentrations are from 5 to 15 wt %, or from 8 to 13 wt %, or from 10 to 11 wt %.

During the quenching, the pH of the mixture may be controlled, since it may be desired that deacylation should be minimised while quenching takes place. This pH control is readily achievable by controlling the addition rate of the aqueous solution of the base while monitoring the pH within the mixture. Any method of pH-controlled addition known to the skilled person may be used.

Suitably, the pH of the mixture is maintained in the range of from about 7.5 to about 10.5 during the quenching, or from about 8.5 to about 10.5, or from about 9.5 to about 10, or from about 9.5 to about 9.75. The pH may also be maintained at a lower level, for example about 4.5, during the addition, and then raised to the desired pH when all of the base has been added. If deacylation is to be carried out as a separate step, though, a pH of more than about 10 should generally be avoided during quenching, since deacylation may then occur. In order to avoid local extremes of pH, the mixture should be adequately mixed throughout the quenching procedure.

The temperature of the mixture during quenching may suitably be maintained in the range of from above 0° C. to about 80° C., for example, in the range of from 10° C. to 60° C., with a range of from about 12° C. to about 35° C. being typical. The quench may be conducted by the "dual stream quench" method, which is described in U.S. Pat. Nos. 5,530,106 and 5,498,709.

In the dual stream process, the quenching conditions are attained by slow addition of the aqueous base with simultaneous slow addition of feed material into a reaction vessel. The reaction vessel can contain an initial charge of an aqueous solution of the tertiary amide such as DMF. Slow addition of aqueous base and feed material allows both the pH and the temperature to be controlled during addition. The feed material and aqueous base are simultaneously added slowly until the desired quantity of feed material has been added. Further aqueous base is added until the desired pH is reached. Then the temperature and pH are maintained at the desired levels for the remainder of the reaction. Generally, the pH should not be permitted to rise above about 10.5 during the course of the quenching reaction.

Quenching may alternatively be carried out by a circulated process. In the circulated process, the quenching conditions are attained by circulating feed mixture from a vessel through a circulation loop. Feed mixture and aqueous base are added slowly into this circulation loop. Slow addition of aqueous base and feed material allows both the pH and the temperature to be controlled during addition. Sufficient aqueous base is added until the desired pH is reached. Then the temperature and pH are maintained at the desired levels for the remainder of the reaction. This process may be run in a batch or continuous mode. Generally, the pH should not be permitted to rise above about 10.5 during the course of the quenching reaction.

Following quenching, the mixture may be neutralised by the addition of aqueous acid, for example aqueous hydrochloric acid. The sucralose-6-acylate can then be isolated by conventional means, if desired, or deacylation can be carried out without isolation of the sucralose-6-acylate.

After quenching, or in a combined process with the quenching, at least a portion of the 4,1',6'-trichloro-4,1',6'-trideoxy-galactosucrose-6-acylate can be deacylated to afford sucralose. The deacylation can be performed before or after the removal of remaining reaction vehicle and/or cosolvent.

The deacylation can be carried out, for example, by the method disclosed in U.S. Pat. No. 6,890,581, incorporated herein in its entirety by reference. Other methods for deacylating sucralose-6-acylates, and for isolating and/or purifying sucralose, are disclosed in U.S. Pat. No. 5,977,349, U.S. Pat. No. 6,943,248, U.S. Pat. No. 6,998,480, U.S. Pat. No. 7,049,435, U.S. Pat. No. 6,809,198, U.S. Pat. No. 6,646,121, U.S. Pat. No. 5,298,611, U.S. Pat. No. 5,498,709, US2006/0188629, US2006/0276639, US2007/0015916, US2007/0160732, and US2007/0270583, the disclosures of which are all incorporated herein by reference.

The deacylation can be carried out by treatment with a base. Any suitable base may be used, and suitable bases are those already mentioned as the base for quenching. For convenience, the same base may be used for deacylation and quenching. Sodium hydroxide may be used as the base in both cases.

In order to effect deacylation, it is necessary to raise the pH of the mixture, typically to a level above that at which the quenching was carried out. In order to minimise decomposition of the tertiary amide reaction vehicle and/or cosolvent (if the deacylation is performed before the removal of remaining reaction vehicle and/or cosolvent), the deacylation may be carried out under carefully controlled conditions.

Therefore, the deacylation is preferably performed at a pH of from 10 to 13.5, or from 10 to 12, or from 10.5 to 11.2, at a temperature of from 60 to 0° C., or from 40 to 0° C., or from 35° C. to 25° C., the higher pH being used with the lower temperature and vice versa.

If the deacylation is carried out after the removal of remaining reaction vehicle and cosolvent, then the deacylation conditions are less critical, although the above described conditions can still be used. In general, the deacylation may be carried out at a pH of from 8 to 14 and a temperature of from 0 to 60° C., or at a pH of from 10 to 12 and a temperature of from 0 to 40° C.

The deacylation reaction can be conveniently monitored by HPLC. For optimum yields, it is important to monitor the progress of the deacylation reaction, and neutralise the mixture when the reaction is complete. The pH of the mixture should be adjusted to from 6 to 8.5, or approximately 7.5. The mixture can conveniently be neutralised using aqueous hydrochloric acid, or using citric acid or acetic acid. Alternatively, the mixture can be neutralised with gaseous carbon dioxide.

The pH control discussed above in relation to deacylation and subsequent neutralisation is more critical at plant scale; on smaller scales the wider ranges of indicated pH can be employed.

The quenching and deacylation can be carried out in a batch or continuous manner and may be carried out in a single vessel or in multiple vessels. Equally, a combination transitioning between continuous and batch from one or more vessels to one or more vessels can be used. The choice of arrangement will be dictated by practical considerations.

Although quenching and deacylation are carried out sequentially in embodiments described above, it is also possible for quenching and deacylation to be carried out together. In this embodiment, the aqueous solution of a base is added to the chlorination product stream exactly as described above for quenching, but with the exception that the pH of the stream is allowed to rise immediately to a level where deacylation can occur, rather than being controlled to minimise deacylation. Suitable pH conditions for effecting deacylation are discussed above, and are equally applicable here.

The removal of remaining reaction vehicle and/or cosolvent can be carried out by means known in the art, such as distillation, distillation under reduced pressure, steam distillation, steam stripping, or by use of an agitated thin film drier or spray drier.

If the removal of the reaction vehicle and/or cosolvent is carried out by steam stripping, then such steam stripping can be carried out as described in EP 0708110. Typically, at least 90% of the reaction vehicle present in the mixture at the end of deacylation (if the removal of the reaction vehicle is carried out after deacylation), or after the quench of the chlorination reaction, (if the removal of the reaction vehicle is carried out before the deacylation) is removed during this step. More typically, at least 99% is removed.

If the mixture is concentrated by distillation, then such distillation will typically remove water and reaction vehicle, and may also remove cosolvent. Solids may precipitate as a result of the distillation. The solids may include salts, for example sodium chloride, and may also include some product (sucralose and/or sucralose-6-acylate). The solids can be filtered and washed with a suitable solvent, for example methanol or ethanol. The solvent such as methanol or ethanol could be removed, for example by flash distillation. This procedure will generally afford the desired sucralose or sucralose-6-acylate in predominantly aqueous medium. The desired product can be isolated by precipitation or by extraction. Extraction can be performed, for example, by using ethyl acetate or methyl tert-butyl ether.

Alternatively or additionally, before or after quenching and/or deacylation, a partitioning solvent may be used to achieve separation of the components of the mixture. For example, addition of a suitable solvent can be used to partition the components. The partitioning solvent can be, for example, ethyl acetate. The partitioning solvent may be employed in a feed:solvent ratio of from 0.5:1 to 1:3, or from 1:1 to 1:2.

Alternatively or additionally, after quenching and/or deacylation, sucralose can be extracted from an aqueous stream using a suitable solvent, such as ethyl acetate or methyl tert-butyl ether.

The reaction vehicle, such as DMF, and the cosolvent including DMAc will generally be removed together from the reaction product mixture. Thus, frequently, a mixture of DMF and DMAc will be obtained. As is disclosed in WO 2010/151489, it will generally be necessary to separate the DMAc from the DMF, before recycling DMF for reuse, because of the interference of DMAc with the first stage chlorination reaction. This can be achieved, for example, by fractional distillation, as disclosed in WO 2010/151489.

Perfluorooctane

Methods relating to the use of perfluorooctane as a cosolvent are described in co-pending application PCT/GB2014/053698, which is incorporated herein by reference in its entirety.

In cases where the cosolvent additionally comprises perfluorooctane, the chlorination mixture during the heating period in step (iv) may be heterogeneous; that is, that it comprises two liquid phases. One phase (which if the reaction vehicle is DMF will usually be the lower phase) will comprise predominantly perfluorooctane, and is referred to herein as the perfluorooctane-rich phase. The other phase is by definition the perfluorooctane-poor phase. The perfluorooctane-poor phase comprises predominantly the reaction vehicle, the chlorinated carbohydrate product and any other cosolvent. The reaction vehicle may be immiscible with the perfluorooctane cosolvent.

In some embodiments of the invention, the perfluorooctane-rich phase can be separated from the rest of the reaction mixture before chlorination quench, that is, after step (iv) and before step (v). This is a particularly useful manner in which the perfluorooctane can be separated and isolated for recovery and reuse.

If desired, a phase transfer catalyst may be included in the mixture. The phase transfer catalyst may be included with the perfluorooctane. Alternatively the phase transfer catalyst may be added separately from the perfluorooctane, in which case it may be added in the first component, in the second component, or during step (iii), or after step (iii) and before step (iv). Phase transfer catalysts are known in the art. The phase catalyst may be a quaternary ammonium or phosphonium salt, for example a halide salt thereof such as a chloride salt. A suitable catalyst is Starks' Catalyst (Aliquat 336), which is a quaternary ammonium salt which contains a mixture of $C_8$ (octyl) and $C_{10}$ (decyl) chains with $C_8$ predominating. Starks' Catalyst is known for its catalytic oxidation of cyclohexene to 1,6-hexanedioic acid, as an alternative to traditional oxidation methods of nitric acid or potassium permanganate. Other suitable phase transfer catalysts include, for example, quaternary alkyl, aryl, or mixed alkyl-aryl ammonium halides such as benzyltriethylammonium chloride, benzyltributylammonium chloride, tributyl methylammonium chloride, benzyltrimethylammonium chloride, tetrabutylammonium chloride, methyltrioctylammonium chloride; crown ethers such as 18-crown-6 and dibenzo-18-crown-6; quaternary alkyl, aryl, or mixed alkyl-aryl phosphonium halides such as trihexyltetradecylphosphonium chloride, tetraphenylphosphonium chloride, and hexadecyltributylphosphonium chloride; imidazolium halide salts such as 1-butyl-2,3-dimethylimidazolium chloride, 1-butyl-3-methylimidazolium chloride, 1,2-dimethylimidazolium chloride, and 2-chloro-1,3-dimethylimidazolinium chloride; and pyridinium halide salts such as 1-hexylpyridinium chloride. In the phase transfer catalysts, the alkyl group is generally an alkyl group having from 1 to 10 carbon atoms; the aryl group is generally an aryl group having from 6 to 10 carbon atoms, and is preferably a phenyl group; the imidazolium halide salts are generally substituted on the imidazole portion by from 1 to 3 substituents selected from alkyl group as just defined, aryl group as just defined, and halogen (preferably fluorine, chlorine or bromine) and the halide is preferably chloride; and the pyridinium halide salts are generally substituted on the pyridine portion by from 1 to 2 substituents, including 1 substituent on the 1-position of the pyridine, selected from alkyl group as just defined, aryl group as just defined, and halogen (preferably fluorine, chlorine or bromine) and the halide is preferably chloride.

When a phase transfer catalyst is used, then the mixture may be triphasic for example after combining the chlorinating agent with the sucrose-6-acylate in step (iii), during the heating in step (iv) or both. The mixture may become biphasic, for example during the heating in step (iv), or after the heating in step (iv) but before the quenching in step (v), or both.

Sulfolane

In cases where the cosolvent additionally comprises sulfolane, the reaction vehicle may be miscible with the sulfolane.

In cases where the cosolvent additionally comprises sulfolane, the cosolvent may be removed by any suitable method including distillation, chromatography (suitably HPLC), steam stripping or in a thin film dryer. In one convenient embodiment in which the cosolvent comprises sulfolane and DMAc, an antisolvent may be added to the mixture after step (iv) and before step (v). In this method, the desired carbohydrate product precipitates in the solid phase, while the majority of the reaction vehicle and cosolvent remain in the liquid phase.

In one embodiment of the invention, in which the cosolvent comprises perfluorooctane, sulfolane and DMAc, the perfluorooctane-rich phase is firstly separated from the perfluorooctane-poor phase, thereby removing the perfluorooctane cosolvent. Secondly, the perfluorooctane-poor phase is treated, before quenching, by addition of an antisolvent which precipitates the chlorinated mass. In this embodiment, the separation of the perfluorooctane-rich phase and the subsequent addition of the antisolvent occurs after step (iv) and before step (v) in the overall reaction scheme. In an alternative embodiment, the perfluorooctane-rich phase may be separated from the perfluorooctane-poor phase after step (iv) and before step (v). Subsequently, and after step (v), the remaining cosolvent components may be removed by any suitable method including distillation, chromatography (suitably HPLC), steam stripping or in a thin film dryer.

When an antisolvent is used, preferably, greater than 80% of the chlorinated carbohydrate product is present in the solid phase. In some embodiments greater than 90% or greater than 95% of the chlorinated carbohydrate product is present in the solid phase.

Preferably, greater than 80% of the reaction vehicle is present in the liquid phase. In some embodiments greater than 90% or greater than 95% of the reaction vehicle is present in the liquid phase.

Preferably, greater than 80% of the sulfolane cosolvent is present in the liquid phase. In some embodiments greater than 90% or greater than 95% of the sulfolane cosolvent is present in the liquid phase.

The remaining sulfolane cosolvent and/or reaction vehicle is in the solid phase after addition of the antisolvent.

The antisolvent is any solvent that can preferentially precipitate the chlorinated carbohydrate product. The antisolvent can be, for example, ethyl acetate or acetone, or mixtures thereof.

After addition of the antisolvent, the solid phase can be separated from the liquid phase, for example by filtration, or by decantation. The remaining reaction vehicle and/or sulfolane cosolvent in the solid phase can be removed by washing the solid phase with antisolvent, and/or by redissolving solid phase first in a suitable dry solvent, such as reaction vehicle, and then addition of antisolvent to precipitate the chlorinated carbohydrate product for a second time. This multiple washing and/or redissolving step with subsequent precipitation process of the solid phase increases sulfolane cosolvent removal efficiency.

The liquid phase will comprise reaction vehicle, sulfolane cosolvent and antisolvent (as herein defined) which can be collected, separated, and recycled for further use. Suitable methods for separating the reaction vehicle, sulfolane cosolvent and antisolvent include distillation.

The solid phase will comprise the chlorinated mass including the desired chlorinated carbohydrate, possibly with residual reaction vehicle, sulfolane cosolvent and/or antisolvent (as herein defined). This can then be quenched as described herein. This step is according to step (v) of the claimed reaction sequence. After quenching, the product can be deacylated to afford sucralose, if desired.

The inventors have also found that a cosolvent consisting essentially of, or consisting entirely of sulfolane can increase the yield and/or efficiency of the reaction. The addition of cosolvent sulfolane (alone or in addition to DMAc) may reduce the overall degradation of DMF to dimethylamine (DMA), which occurs during second stage of chlorination reaction (See, for example, WO 2010/112813.) It has been found that quenched chlorinated product after chlorination in the presence of cosolvent sulfolane exhibited less DMA than a control experiment without sulfolane. The DMA in the quenched chlorinated product is generally inversely proportional to sulfolane to DMF ratio.

EXAMPLES

Arnold's Reagent, chlorodimethylformiminium chloride, CAS 3724-43-4, was purchased from Sigma Aldrich. DMAc was purchased from Merck. All solvents and chemicals were used as is.

A stock solution of sucrose-6-acetate has the following composition.

| Stock solution 1 | |
| --- | --- |
| Description | % of total, w/w |
| Sucrose-6-acetate | 29.80 |
| Other carbohydrates | 4.43 |
| DMAc (Dimethyl acetamide) | 0.36 |

-continued

Stock solution 1

| Description | % of total, w/w |
|---|---|
| Water | 0.16 |
| Acetic acid | 0.68 |
| DMF (Dimethyl formamide) | Remaining |

A typical composition of the DMF is as follows:

| Description | % of total, w/w |
|---|---|
| DMAc (Dimethyl acetamide) | 0.23 |
| Water | 0.025 |
| DMF (Dimethyl formamide) | Remaining |

Control Experiment without Cosolvent
Ratio DMF:Carbohydrate=7.3:1

A jacketed 500 ml multi-neck reaction flask, equipped with overhead stirrer, thermometer, addition funnel, inert gas (nitrogen) inlet, and condenser was charged with 25.35 g of commercial Arnold's Reagent (purity of 95.0%) and with 45.01 g of DMF. The obtained off-white to yellow colored slurry was cooled to 0-5° C. and then 24.82 g of a sucrose-6-acetate (29.80% wt.) stock solution in DMF (from stock solution described above) was added to the slurry over a period of 15-30 min after which the reaction mass was heated to room temperature and kept at 25° C. for 2 h resulting in homogeneous orange to light brown reaction mixture. Then the mixture was heated to an internal temperature of 100° C. over a period of 45 min and held at this temperature for 11 h. After completion of the chlorination reaction, and cooling of the mixture down to room temperature, dual stream quench was performed using 11% NaOH at pH 9.9 and 15° C., while simultaneous deacylation steps were performed by using 32% NaOH (aq.) at pH 12.1 and 30° C. Then the quenched mixture was neutralized to pH 8.0 with HCl (33% wt.).

Figure 2:
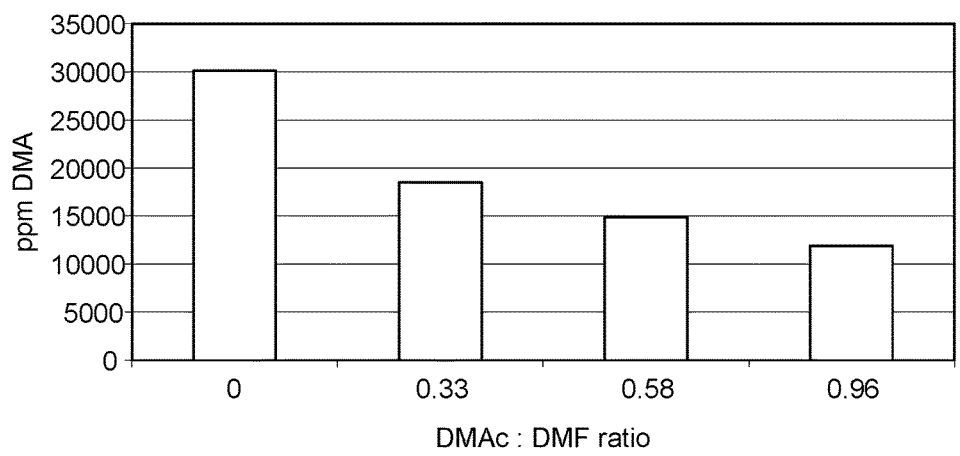
FIG. 2 shows the effect of ratio by weight of DMAc to DMF on the dimethylamine (DMA) formation.

Samples were assayed by HPLC to give 68.0% molar sucralose yield from combining sucralose-6-acetate, sucralose, and 3',6'-anhydro-4,1'-dichloro-4,1'-dideoxy-galactosucralose (shown in FIG. 1), and by ion chromatography to give 30169 ppm DMA (shown in FIG. 2).

Example 1—Chlorination with DMAc Cosolvent

Ratio DMF:Carbohydrate=5.5:1 and DMF:DMAc=1:0.33

A jacketed 500 mL multi-neck reaction flask, equipped with overhead stirrer, thermometer, addition funnel, inert gas (nitrogen) inlet, and condenser was charged with 23.31 g of commercial Arnold's Reagent (purity of 95.0%) and with 27.35 g of DMF. The obtained off-white to yellow colored slurry was cooled to 0-5° C. and then 22.83 g of a sucrose-6-acetate (29.80% wt.) stock solution in DMF (from stock solution described above) was added to the slurry over a period of 15-30 min. after which the reaction mass was heated to room temperature and kept at 25° C. for 2 h. Then, the resulting homogeneous orange to light brown reaction mixture was heated to 100° C. over a period of 45 min; 14.08 g DMAc (purity of >99% containing 0.18 wt. % water) was added when the mixture temperature was in the range 60-65° C. DMF to co-solvent ratio was approximately ~1:0.33. The internal temperature was held at this temperature for 11 h. After completion of the chlorination reaction, and cooling of the mixture down to room temperature, dual stream quench was performed using 11% NaOH at pH 9.9 and 15° C. while simultaneous deacylation steps were performed by using 32% NaOH (aq.) at pH 12.1 and 30° C. Then the quenched mixture was neutralized to pH 8.0 with HCl (33% wt.).

Samples were assayed by HPLC to give 69.1% molar sucralose yield from combining sucralose-6-acetate, sucralose, and 3',6'-anhydro-4,1'-dichloro-4,1'-dideoxy-galactosucralose (shown in FIG. 1), and by IC to give 18545 ppm DMA (shown in FIG. 2).

In this experiment, the addition of DMAc gave an increase of sucralose yield of over 1% compared with the control experiment.

Example 2—Chlorination with DMAc Cosolvent

Ratio DMF:Carbohydrate=4.6:1 and DMF:DMAc=1:0.58

A jacketed 500 mL multi-neck reaction flask, equipped with overhead stirrer, thermometer, addition funnel, inert gas (nitrogen) inlet, and condenser was charged with 23.26 g of commercial Arnold's Reagent (purity of 95.0%) and with 20.27 g of DMF. The obtained off-white to yellow colored slurry was cooled to 0-5° C. and then 22.78 g of a sucrose-6-acetate (29.80% wt.) stock solution in DMF (from stock solution described above) was added to the slurry over a period of 15-30 min. after which the reaction mass was heated to room temperature and kept at 25° C. for 2 h. Then, the resulting homogeneous orange to light brown reaction mixture was heated to 100° C. over a period of 45 min; 21.07 g DMAc (purity of >99% containing 0.18 wt. % water) was added when the mixture temperature was in the range 60-65° C. DMF to co-solvent ratio was approximately ~1:0.58. The internal temperature was held at this temperature for 11 h. After completion of the chlorination reaction, and cooling of the mixture down to room temperature, dual stream quench was performed using 11% NaOH at pH 9.9 and 15° C. while simultaneous deacylation steps were performed by using 32% NaOH (aq.) at pH 12.1 and 30° C. Then the quenched mixture was neutralized to pH 8.0 with HCl (33% wt.).

Samples were assayed by HPLC to give 68.3% molar sucralose yield from combining sucralose-6-acetate, sucralose, and 3',6'-anhydro-4,1'-dichloro-4,1'-dideoxy-galactosucralose (shown in FIG. 1), and by ion chromatography to give 14855 ppm DMA (shown in FIG. 2).

In this experiment, the addition of DMAc did only marginally increase sucralose yield compared with the control experiment.

Example 3—Chlorination with DMAc Cosolvent

Ratio DMF:Carbohydrate=3.7:1 and DMF:DMAc=1:0.96

A jacketed 500 mL multi-neck reaction flask, equipped with overhead stirrer, thermometer, addition funnel, inert gas (nitrogen) inlet, and condenser was charged with 25.13 g of commercial Arnold's Reagent (purity of 95.0%) and with 14.33 g of DMF. The obtained off-white to yellow colored slurry was cooled to 0-5° C. and then 24.60 g of a sucrose-6-acetate (29.80% wt.) stock solution in DMF (from stock solution described above) was added to the slurry over a period of 15-30 min. after which the reaction mass was heated to room temperature and kept at 25° C. for 2 h. Then, the resulting homogeneous orange to light brown reaction mixture was heated to 100° C. over a period of 45 min; 30.32 g DMAc (purity of >99% containing 0.18 wt. % water) was added when the mixture temperature was in the range 60-65° C. Due to a slight drop in the mixture temperature on addition of DMAc, fine white crystals formed which dissolved as the temperature increased to above 60° C. DMF to co-solvent ratio was approximately ~1:0.96. The internal temperature was held at this temperature for 11 h. After completion of the chlorination reaction, and cooling of the mixture down to room temperature, dual stream quench was performed using 11% NaOH at pH 9.9 and 15° C. while simultaneously deacylation steps were performed by using 32% NaOH (aq.) at pH 12.1 and 30° C. Then the quenched mixture was neutralized to pH 8.0 with HCl (33% wt.).

Samples were assayed by HPLC to give 70.2% molar sucralose yield from combining sucralose-6-acetate, sucralose, and 3',6'-anhydro-4,1'-dichloro-4,1'-dideoxy-galactosucralose (shown in FIG. 1), and by ion chromatography to give 11888 ppm DMA (shown in FIG. 2).

In this experiment, the addition of DMAc gave an increase of sucralose yield of over 2% compared with the control experiment.

In the second control example, examples 4-6 and the comparative examples (all below) the reagents used were as follows; Arnold's Reagent, chlorodimethylformiminium chloride, CAS 3724-43-4, perfluorooctane, and sulfolane, which were purchased from Sigma Aldrich. DMAc was purchased from Merck. All solvents and chemicals were used as is.

Another stock solution of sucrose-6-acetate has the following composition and was used in the second control example, examples 4-6 and the comparative examples (all below).

| Stock solution 2 | |
|---|---|
| Description | % of total, w/w |
| Sucrose-6-acetate | 36.93 |
| Other carbohydrates | 5.54 |
| DMAc (Dimethyl acetamide) | 0.33 |
| Water | 0.09 |
| Acetic acid | 0.67 |
| DMF (Dimethyl formamide) | Remaining |

A typical composition of the DMF is as follows:

| Description | % of total, w/w |
|---|---|
| Water | 0.16 |
| DMF (Dimethyl formamide) | Remaining |

Control Experiment 2 without Cosolvent
Ratio DMF:Carbohydrate=12:1

A jacketed 500 ml multi-neck reaction flask, equipped with overhead stirrer, thermometer, addition funnel, inert gas (nitrogen) inlet, and condenser was charged with 25.40 g of commercial Arnold's Reagent (purity of 95.0%) and with 91.80 g of DMF. The obtained off-white to yellow coloured slurry was cooled to 0-5° C. and then 19.85 g of a sucrose-6-acetate (36.93% wt.) stock solution in DMF (from stock solution described above) was added to the slurry over a period of 15-30 min after which the reaction mass was heated to room temperature and kept at 25° C. for 2 h resulting in homogeneous orange to light brown reaction mixture. Then the mixture was heated to an internal temperature of 100° C. over a period of 45 min and held at this temperature for 11 h. After completion of the chlorination reaction, and cooling of the mixture down to room temperature, dual stream quench was performed using 11% NaOH at pH 9.9. Then the quenched mixture was neutralized to pH 8.5 with HCl (33% wt.).

Samples were assayed by HPLC to give 62.0% molar sucralose yield from combining sucralose-6-acetate and sucralose, and by ion chromatography (IC) to give 16252 ppm DMA.

Example 4—Chlorination with Sulfolane and DMAc Cosolvent Combination

Ratio DMF:Carbohydrate=4:1, DMF:Sulfolane=1:1, and DMF:DMAc=1:1

A jacketed 500 mL multi-neck reaction flask, equipped with overhead stirrer, thermometer, addition funnel, inert gas (nitrogen) inlet, and condenser was charged with 25.40 g of commercial Arnold's Reagent (purity of 95.0%), with 22.28 g of DMF, and with 34.64 g sulfolane. The obtained off-white to yellow colored slurry was cooled to 0-5° C. and then 20.39 g of a sucrose-6-acetate (36.93% wt.) stock solution in DMF (from stock solution described above) was added to the slurry over a period of 15-30 min. after which the reaction mass was heated to room temperature and kept at 25° C. for 2 h. Then the resulting homogeneous orange to light brown reaction mass was heated to 100° C. over a period of 45 min. To the resulting dark colored reaction mixture 34.64 g DMAc (purity of >99% containing 0.18 wt. % water) was added. DMF to sulfolane ratio was approximately ~1:1 and DMF to DMAc ratio was approximately ~1:1. The internal temperature was held at this temperature (100° C.) for 11 h. After completion of the chlorination reaction, and cooling of the mixture down to room temperature, dual stream quench was performed using 11% NaOH at pH 9.9 and 15° C. Then the quenched mixture was neutralized to pH 8.5 with HCl (33% wt.).

Samples were assayed by HPLC to give 63.3% molar sucralose yield from combining sucralose-6-acetate and sucralose, and by IC to give 2891 ppm DMA.

In this experiment, the addition of DMAc and sulfolane gave an increase of sucralose yield of over 1% compared with the control experiment.

Example 5—Chlorination with Perfluorooctane and DMAc Cosolvent Combination

Ratio DMF:Carbohydrate=4:1, DMF:Perfluorooctane=1:1, and DMF:DMAc=1:1

A jacketed 500 mL multi-neck reaction flask, equipped with overhead stirrer, thermometer, addition funnel, inert gas (nitrogen) inlet, and condenser was charged with 24.82 g of commercial Arnold's Reagent (purity of 95.0%) and with 21.76 g of DMF. The obtained off-white to yellow colored slurry was cooled to 0-5° C. and then 19.92 g of a sucrose-6-acetate (36.93% wt.) stock solution in DMF (from stock solution described above) was added to the slurry over a period of 15-30 min. after which the reaction mass was heated to room temperature and kept at 25° C. for 2 h. Then 33.84 g perfluorooctane was added to the resulting homogeneous orange to light brown reaction mass and then the reaction mixture was heated to 100° C. over a period of 45 min. To the resulting dark colored reaction mixture 33.84 g DMAc (purity of >99% containing 0.18 wt. % water) was added. DMF to perfluorooctane ratio was approximately ~1:1 and DMF to DMAc ratio was approximately ~1:1. The internal temperature was held at this temperature (100° C.) for 11 h. After completion of the chlorination reaction and cooling of the mixture down to room temperature, the perfluorooctane and the chlorination mixture were two separate phases. Perfluorooctane, a clear heavy phase separating at the bottom of the reactor, was discharged from the drain of the reactor, and was collected separately (weight of perfluorooctane was 29.1 g, with 86.1% recovery without work-up). The top phase, which was dark colored chlorination mixture, was dual stream quenched using 11% NaOH at pH 9.9 and 15° C. Then the quenched mixture was neutralized to pH 8.5 with HCl (33% wt.).

Samples were assayed by HPLC to give 63.9% molar sucralose yield from combining sucralose-6-acetate and sucralose, and by IC to give 3647 ppm DMA.

In this experiment, the addition of DMAc and perfluoroctane gave an increase of sucralose yield of almost 2% compared with the control experiment.

Example 6—Chlorination with Sulfolane, Perfluorooctane and DMAc Cosolvent Combination Ratio DMF:Carbohydrate=4:1, DMF:Sulfolane=1:0.67, DMF:Perfluorooctane=1:0.55 and DMF:DMAc=1:0.67

A jacketed 500 mL multi-neck reaction flask, equipped with overhead stirrer, thermometer, addition funnel, inert gas (nitrogen) inlet, and condenser was charged with 24.79 g of commercial Arnold's Reagent (purity of 95.0%) and with 21.74 g of DMF and with 22.65 g sulfolane. The obtained off-white to yellow colored slurry was cooled to 0-5° C. and then 19.90 g of a sucrose-6-acetate (36.93% wt.) stock solution in DMF (from stock solution described above) was added to the slurry over a period of 15-30 min. after which the reaction mass was heated to room temperature and kept at 25° C. for 2 h. Then 18.60 g perfluorooctane was added to the resulting homogeneous orange to light brown reaction mass and the reaction mixture was heated to 100° C. over a period of 45 min. To the resulting dark colored reaction mixture 22.65 g DMAc (purity of >99% containing 0.18 wt. % water) was added. DMF to sulfolane ratio was approximately ~1:0.67, DMF to perfluorooctane ratio was approximately ~1:0.55 and DMF to DMAc ratio was approximately ~1:0.67. The internal temperature was held at this temperature (100° C.) for 11 h. After completion of the chlorination reaction and cooling of the mixture down to room temperature, the perfluorooctane and the chlorination mixture were two separate phases. Perfluorooctane, a clear heavy phase separating at the bottom of the reactor, was discharged from the drain of the reactor, and was collected separately (weight of perfluorooctane was 14.75 g, with 79.3% recovery without work-up). The top phase, which was dark colored chlorination mixture, was dual stream quenched using 11% NaOH at pH 9.9 and 15° C. Then the quenched mixture was neutralized to pH 8.5 with HCl (33% wt.).

Samples were assayed by HPLC to give 67.6% molar sucralose yield from combining sucralose-6-acetate and sucralose, and by IC to give 6449 ppm DMA.

In this experiment, the addition of DMAc, sulfolane and perfluorooctane gave an increase of sucralose yield of over 5% compared with the control experiment.

Comparative Examples

Stock solution 2 was used in the comparative examples (all below). In the comparative examples, it is believed that unreacted Arnold's reagent was present in solution when DMAc was added.

Comparative Example 1—Chlorination with Sulfolane and DMAc Cosolvents Combination Ratio DMF:Carbohydrate=4:1, DMF:Sulfolane=1:1, and DMF:DMAc=1:1

A jacketed 500 mL multi-neck reaction flask, equipped with overhead stirrer, thermometer, addition funnel, inert gas (nitrogen) inlet, and condenser was charged with 24.13 g of commercial Arnold's Reagent (purity of 95.0%), with 21.17 g of DMF, and with 33.02 g sulfolane. The obtained off-white to yellow colored slurry was cooled to 0-5° C. and then 18.86 g of a sucrose-6-acetate (36.93% wt.) stock solution in DMF (from stock solution described above) was added to the slurry over a period of 15-30 min. after which the reaction mass was heated to room temperature and kept at 25° C. for 2 h. Then, the mixture was heated to 100° C. over a period of 45 min; 33.02 g DMAc (purity of >99% containing 0.18 wt. % water) was added when the mixture temperature was in the range 60-65° C. Due to a slight drop in the mixture temperature on addition of DMAc, white solids precipitated forming a slurry. The white solids dissolved as the temperature increased to above 60° C. DMF to sulfolane ratio was approximately ~1:1 and DMF to DMAc ratio was approximately ~1:1. The internal temperature was held at this temperature (100° C.) for 11 h. After completion of the chlorination reaction, and cooling of the mixture down to room temperature, dual stream quench was performed using 11% NaOH at pH 9.9 and 15° C. Then the quenched mixture was neutralized to pH 8.5 with HCl (33% wt.). Samples were assayed by HPLC to give 57.27% molar sucralose yield from combining sucralose-6-acetate and sucralose, and by IC to give 2352 ppm DMA.

In another comparative experiment, the above process was repeated except that DMAc was added at the end of the 2 hour hold at 25° C. and before heating to 100° C. was initiated (instead of DMAc addition at 60-65° C.). Samples were assayed by HPLC to give 51.13% molar sucralose yield from combining sucralose-6-acetate and sucralose, and by IC to give 887 ppm DMA.

Comparative Example 2—Chlorination with Perfluorooctane and DMAc Cosolvent Combination Ratio DMF:Carbohydrate=4:1, DMF:Perfluorooctane=1:1, and DMF:DMAc=1:1

A jacketed 500 mL multi-neck reaction flask, equipped with overhead stirrer, thermometer, addition funnel, inert gas (nitrogen) inlet, and condenser was charged with 26.40 g of commercial Arnold's Reagent (purity of 95.0%) and with 23.16 g of DMF. The obtained off-white to yellow colored slurry was cooled to 0-5° C. and then 20.63 g of a sucrose-6-acetate (36.93% wt.) stock solution in DMF (from stock solution described above) was added to the slurry over a period of 15-30 min. after which the reaction mass was heated to room temperature and kept at 25° C. for 2 h. Then 36.12 g perfluorooctane was added to the resulting homogeneous orange to light brown reaction mass. Then, the mixture was heated to 100° C. over a period of 45 min; 36.12 g DMAc (purity of >99% containing 0.18 wt. % water) was added when the mixture temperature was in the range 60-65° C. Due to a slight drop in the mixture temperature on addition of DMAc, whereby white solids precipitated forming a slurry. The white solids dissolved as the temperature increased to above 60° C. DMF to perfluorooctane ratio was approximately ~1:1 and DMF to DMAc ratio was approximately ~1:1. The internal temperature was held at this temperature (100° C.) for 11 h. After completion of the chlorination reaction and cooling of the mixture down to room temperature, the perfluorooctane and the chlorination mixture were two separate phases. Perfluorooctane, a clear heavy phase separating at the bottom of the reactor, was discharged from the drain of the reactor, and was collected separately (weight of perfluorooctane was 32.19 g, with 89.1% recovery without work-up). The top phase, which was dark colored chlorination mixture, was dual stream quenched using 11% NaOH at pH 9.9 and 15° C. Then the quenched mixture was neutralized to pH 8.5 with HCl (33% wt.). Samples were assayed by HPLC to give 55.07% molar sucralose yield from combining sucralose-6-acetate and sucralose, and by IC to give 3269 ppm DMA.

In another comparative experiment, the above process was repeated except that DMAc was added at the end of the 2 hour hold at 25° C. and before heating to 100° C. was initiated (instead of DMAc addition at 60-65° C.). Samples were assayed by HPLC to give 50.30% molar sucralose yield from combining sucralose-6-acetate and sucralose.

Comparative Example 3—Chlorination with Sulfolane, Perfluorooctane and DMAc Cosolvent Combination Ratio DMF:Carbohydrate=4:1, DMF:Sulfolane=1:0.68, DMF:Perfluorooctane=1:0.55, and DMF:DMAc=1:0.67

A jacketed 500 mL multi-neck reaction flask, equipped with overhead stirrer, thermometer, addition funnel, inert gas (nitrogen) inlet, and condenser was charged with 23.64 g of commercial Arnold's Reagent (purity of 95.0%) and with 20.74 g of DMF and with 21.67 g sulfolane. The obtained off-white to yellow colored slurry was cooled to 0-5° C. and then 18.47 g of a sucrose-6-acetate (36.93% wt.) stock solution in DMF (from stock solution described above) was added to the slurry over a period of 15-30 min. after which the reaction mass was heated to room temperature and kept at 25° C. for 2 h. Then 17.79 g perfluorooctane was added to the resulting homogeneous orange to light brown reaction mass. Then, the mixture was heated to 100° C. over a period of 45 min; 21.67 g DMAc (purity of >99% containing 0.18 wt. % water) was added when the mixture temperature was in the range 60-65° C. Due to a slight drop in the mixture temperature on addition of DMAc, white solids precipitated forming a slurry. The white solids dissolved as the temperature increased to above 60° C. DMF to sulfolane ratio was approximately ~1:0.67, DMF to perfluorooctane ratio was approximately ~1:0.55 and DMF to DMAc ratio was approximately ~1:0.67. The internal temperature was held at this temperature (100° C.) for 11 h. After completion of the chlorination reaction and cooling of the mixture down to room temperature, the perfluorooctane and the chlorination mixture were two separate phases. Perfluorooctane, a clear heavy phase separating at the bottom of the reactor, was discharged from the drain of the reactor, and was collected separately (weight of perfluorooctane was 13.15 g, with 73.9% recovery without work-up). The top phase, which was dark colored chlorination mixture, was dual stream quenched using 11% NaOH at pH 9.9 and 15° C. Then the quenched mixture was neutralized to pH 8.5 with HCl (33% wt.). Samples were assayed by HPLC to give 61.44% molar sucralose yield from combining sucralose-6-acetate and sucralose, and by IC to give 3512 ppm DMA.

In another comparative experiment, the above process was repeated except that DMAc was added at the end of the 2 hour hold at 25° C. and before heating to 100° C. was initiated (instead of DMAc addition at 60-65° C.). Samples were assayed by HPLC to give 49.90% molar sucralose yield from combining sucralose-6-acetate and sucralose, and by IC to give 3367 ppm DMA.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A method for the chlorination of a sucrose-6-acylate to produce a 4,1',6'-trichloro-4,1',6'-trideoxy-galactosucrose-6-acylate, wherein said method comprises the following steps (i) to (v):
    (i) providing a first component comprising sucrose-6-acylate;
    (ii) providing a second component comprising a chlorinating agent;
    (iii) combining said first component and said second component to afford a mixture;
    (iv) heating said mixture for a heating period in order to provide chlorination of sucrose-6-acylate at the 4, 1' and 6' positions thereof;
    (v) quenching said mixture to produce a 4,1',6'-trichloro-4,1',6'-trideoxy-galactosucrose-6-acylate;
    wherein at least one of said first component and said second component comprises dimethylformamide (DMF); and
    wherein dimethylacetamide (DMAc) is added to said mixture either (a) after step (iii) and before step (iv) or (b) during step (iv).

2. The method according to claim 1, wherein both of said first component and said second component comprise dimethylformamide (DMF).

3. The method according to claim 1, wherein said mixture additionally comprises sulfolane and/or perfluorooctane during at least a portion of the heating period of step (iv).

4. The method according to claim 1, wherein at least one of DMAc, sulfolane, perfluorooctane, or a mixture thereof is added to the mixture after step (iii) and before step (iv).

5. The method according to claim 1, wherein at least one of DMAc, sulfolane, perfluorooctane, or a mixture thereof is added to the mixture during step (iv).

6. The method according to claim 5, wherein the at least one of DMAc, sulfolane, perfluorooctane, or a mixture thereof is added once the mixture temperature Is greater than or equal to about 55° C.

7. The method according to claim 3, wherein;
    the DMAc is added to the mixture after step (iii) and before step (iv) and/or during step (iv); and
    the perfluorooctane and/or sulfolane is present in the first and/or second components, and/or is added during step (iii).

8. The method according to claim 7 wherein the DMAc is added to the mixture during step (iv) once the mixture temperature is greater than or equal to about 55° C.

9. The method according to claim 1, wherein one of DMAc, or DMAc and perfluorooctane, or DMAC and sulfolane or DMAc, perfluorooctane and sulfolane is present in the mixture during at least a portion of the heating period of step (iv).

10. The method according to claim 1, which further comprises a step (vi) of converting at least a portion of said 4,1',6'-trichloro-4,1',6'-trideoxy-galactosucrose-6-acylate to sucralose.

11. The method according to claim 10, which further comprises a step (vii) of isolating and purifying the sucralose.

\* \* \* \* \*